May 1, 1956 J M ALLRED, JR. Plant Pat. 1,474
AVOCADO TREE
Filed Feb. 24, 1953
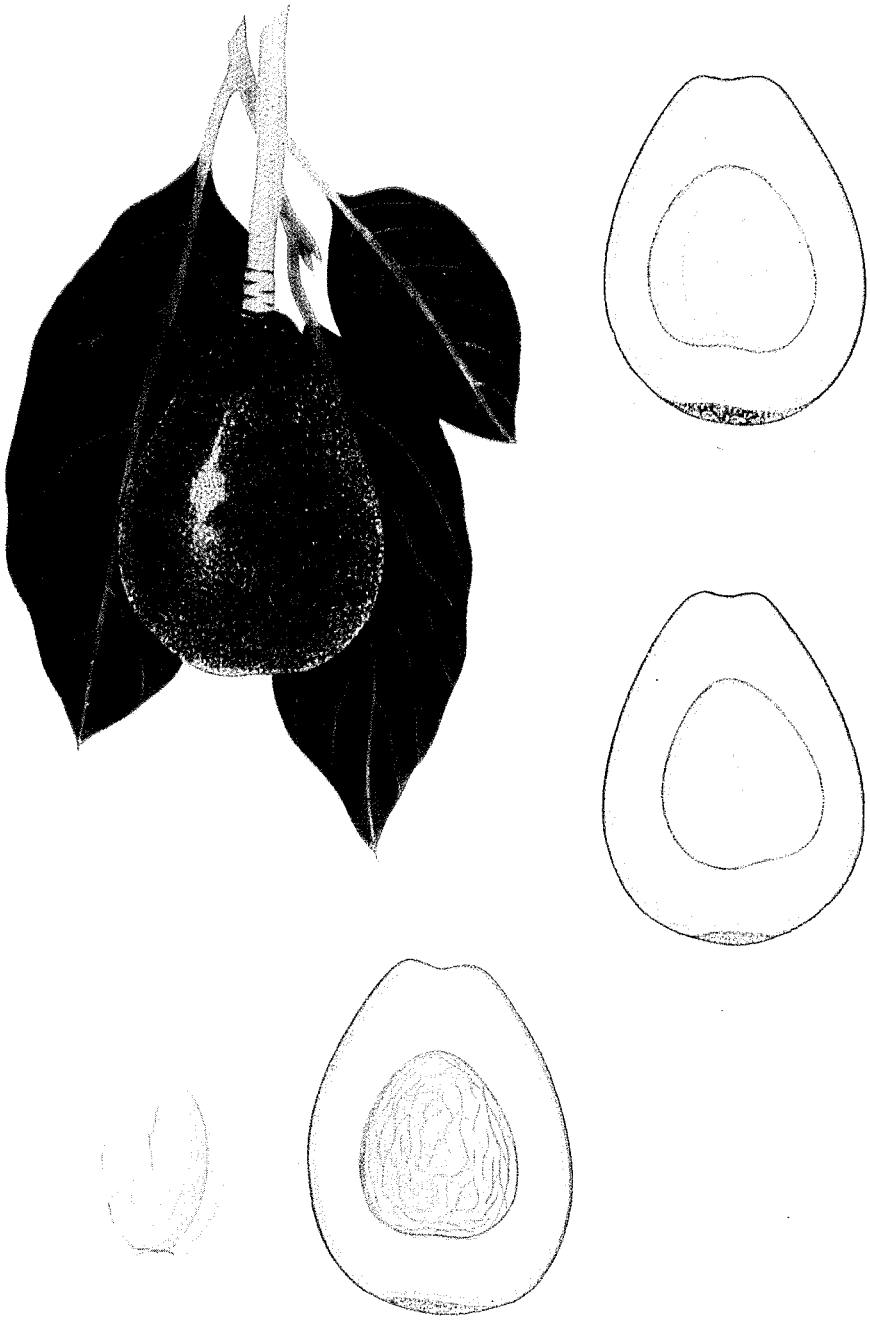
INVENTOR.
J M ALLRED JR.
BY J. F. Cumes
ATTORNEY United States Patent Office Plant Pat. 1,474
Patented May 1, 1956

1,474

AVOCADO TREE

J M Allred, Jr., Baldwin Park, Calif.

Application February 24, 1953, Serial No. 338,631

1 Claim. (Cl. 47—62)

My discovery relates to a new and distinct avocado tree which is an improvement over previously known varieties. The tree withstands frost exceptionally well and produces excellent marketable fruit that mature during October.

Due to some characteristics of the fruit and tree it has been established that it is from the Mexican race of avocados. The parent plant was discovered by me on my own property located at 15250 Arrow Highway in the city of Baldwin Park, California, as a small shoot or "sport" coming from the root or lower portion of the trunk near the ground of a small tree that had been badly sunburned and the trunk had died. When the shoot was about two feet tall the top growth was eaten by grazing animals. After this topping it started to vigorously grow additional branches in 1946.

No attention was paid to this tree until the extremely cold spell that occurred in this area in January 1949. Large Fuerte and Ryan trees, well known unpatented varieties of avocadoes, surrounding the parent tree froze most of the wood that was less than one inch in diameter. The parent tree was at this time about six feet tall and all of its wood escaped damage from the freeze; the tree did not shed any leaves as a result of the freeze. Immediately after the freezing spell ended, the tree bloomed and set fruit. Only one fruit reached maturity in 1949, but in 1950 the tree produced approximately 30 pounds of fruit. In 1951 the production of fruit was about 25 pounds and in 1952 the tree produced about 64 pounds of fruit.

The tree bears a good average sized fruit that matures between September 20 and November 15. This is particularly desirable since at this time of the year there are no good avocados maturing. The tree has good growth habits and the general appearance of the fruit is excellent. The fruit has substantially no neck and is practically free from fiber. The fruit keeps well and no internal rotting occurs prior to full maturity of the fruit.

The characteristics of the tree and fruit vary slightly under various conditions of climate, moisture, topography, soil, and care but the desirable characteristics are present under all growing conditions.

This new variety has been successfully reproduced by budding and grafting by employing thin skinned Mexican seedlings as root stock at 15250 Arrow Highway in Baldwin Park, California.

The terminal foliage as well as the fruit stem and button of the new variety of avocado is illustrated in the appended drawing which also includes illustrations showing the manner in which the seed is positioned in the fruit, the thickness of the seed skin, the seed cavity and the general appearance of the seed. To facilitate identification of the colors which are described in the specification, the plate number, letter and number classification of the color, as it is listed in "A Dictionary of Color," by A. Maerz and M. Rea Paul, 1930 Edition, published by McGraw-Hill Book Co. Inc., is included following the more general description.

THE TREE

*Growth habits*

The tree is semi-upright having its long branches growing out from the trunk and substantially perpendicular to it. The tree is about 15 feet high, has a good subterranean root system and is characterized by the rapid growth of budded or grafted stock.

*Bearing habits and blossoming*

The fruit is of average size and weight and there is a tendency for the tree to overbear. The tree starts to bloom in March, the blossoms appearing in large pods. Almost every flower will set a fruit about the middle of April. The tree then drops off the excess fruit gradually during the summer until the number of fruit correspond to the quantity the tree can support.

*Hardiness*

The tree withstands cold weather exceptionally well. During the exceptionally cold spell in this area that occurred in the winter of 1949 the parent tree did not show any indications of frostbite even though the temperature dropped to as low as 20° F. for a long period of time. During the same period large Fuerte and Ryan trees, unpatented varieties of avocados growing all around the parent tree had all branches under one inch in diameter frozen. This antifreezing characteristic is also found to exist in young grafts.

*Maturity*

The grafted or budded trees start bearing at an early age. About two and one-half years after grafting the trees will produce an appreciable quantity of mature fruit.

*Fruit placement*

The fruit is well distributed about the tree. The fruit hangs pendant on a green stem usually about 2½ inches in length until the fruit beings to mature. At this time the stems turn a yellowish light green color, Plate 17–L–7. About 10% of the stems are forked and support two fruit growing side by side.

*Ripening date*

The fruit matures from September 20 to November 15.

*Foliage*

*Quantity.*—Abundant foliage with light drop during blooming and fruit setting time.

*Color.*—The mature leaves are a deep shade of green, Plate 23–J–7 on the upper side and are distinguishable from other varieties even at a distance. The lower surface of the leaves is a lighter shade of green, Plate 21–H–5 than the upper surface. The color of the mature leaves varies slightly during the different seasons.

*Size.*—The leaves are from 5 inches to 7 inches long and are between 3 inches and 3½ inches wide.

*Shape.*—Normal, with the edges waved or rippled.

*Texture and veining.*—The leaf as a whole is smooth and not puckered. The upper surface is smooth and semi-glossy. The leaf veins and stems are lighter green in color, Plate 22–L–1, than the remainder of the leaf. The principal leaf veins are quite pronounced while the minor veins are less distinct. The leaves have 8 to 11 ribs with the midrib relatively straight where normal growth has occurred.

*Distribution.*—The leaves are well distributed over the tree and afford protection to the fruit.

THE FRUIT

*Weight*

The fruit weigh between 4 ounces and 8 ounces; the average fruit will weigh about 5½ ounces.

*Shape*

The fruit is ovoid in shape measuring about 3¼ inches in length and 2½ inches in width at the base. A characteristic of the fruit is that at the stem end and uniformly surrounding the button, that is normally quite small, there is an area that is almost annular in contour. This annular or blunt portion is generally substantially perpendicular to the longitudinal axis of the fruit as shown in the drawings.

*Skin*

The color of the skin is common to the green Mexican varieties. The skin is medium green, Plate 24–L–1, speckled with very light yellowish green, Plate 21–L–4, specks that are close together at the lower end of the fruit and become progressively less pronounced and are further apart as the stem end is approached. A tiny brown speck, Plate 15–E-12, is sometimes observed near the center of the light green specks, Plate 21–L–4. The medium green background color becomes a little darker about one-half inch from the button and on the surface adjoining the button there are substantially no specks. No rust appears on the skin.

*Aspect*

The skin is smooth but no glossy.

*Texture*

The skin of the fruit is thin, pliant but very tough. The skin adheres tightly to the flesh and does not sag, crack or check when the fruit is green or when it is ripe.

*Button*

The button is small and partly buried in a slight depression centrally located at the flattened end of the fruit. The color of the button is yellowish green, Plate 17–L–7, when the fruit is mature. The button is firmly attached to the stem and the stem attachment to the tree is strong so that the fruit is not displaced by wind.

*Flesh*

*Color.*—The flesh is a rich yellow, Plate 18–K–1, gradually blending into a light green, Plate 21–L–5, coloration near the skin.

*Flavor.*—The flavor is nutty and is similar to a Fuerte and is rated a Good Plus.

*Texture.*—The flesh has a butter-like consistency with practically no fiber content.

*Oil content.*—The fruit has approximately 8% oil in the later part of September and the oil content increases to approximately 17% during the last week of October or the first part of November.

*Seed*

*Shape.*—Generally oval in some cases almost round with a few pronounced wrinkles on the outer surface.

*Size.*—The average seed is about 27% of the total weight of the fruit.

*Texture.*—The seed is a rich yellow, Plate 10–F–6, in color and is quite smooth. The seed is relatively soft and can be cut with a knife.

*Seed coat.*—The seed coat is a light brown, Plate 12–D–10, when the fruit is mature, is relatively thick, as shown in the drawing, and adheres to the seed.

*Separability.*—The seed coat does not adhere to the flesh surrounding the seed cavity. This sometimes causes the seed to rattle within the seed cavity when the fruit is shaken. Loose seeds occur in about 20% of the fruit.

Having thus described my invention I claim:

The new and distinct variety of avocado tree substantially as herein shown and described, distinguished as to novelty, by its ripening period in the early fall; medium sized fruit of medium green background speckled with light yellowish green specks that are close together at the lower end of the fruit and become less pronounced and further apart as the stem end is approached, disappearing almost entirely at the immediate area surrounding the button, when fruit is fully matured; having a skin that is thin, pliant, tough, and smooth but not glossy, the skin adhering tightly to the flesh; the fruit borne on short length stems; the fruit having a medium size relatively loose seed, and rich yellow flesh that gradually changes to a light green color near the skin, has practically no fiber, and has a butter-like consistency.

No references cited.